United States Patent [19]

Hughes

[11] Patent Number: 4,985,062

[45] Date of Patent: * Jan. 15, 1991

[54] METHOD OF IMPROVING CROP YIELD

[75] Inventor: John Hughes, Arlington Heights, Ill.

[73] Assignee: American Colloid Company, Arlington Heights, Ill.

[ * ] Notice: The portion of the term of this patent subsequent to Jun. 30, 2004 has been disclaimed.

[21] Appl. No.: 394,958

[22] Filed: Aug. 17, 1989

Related U.S. Application Data

[63] Continuation-in-part of Ser. No. 926,210, Nov. 3, 1986, Pat. No. 4,906,276.

[51] Int. Cl.$^5$ .............................................. A01N 33/00
[52] U.S. Cl. ............................................ 71/77; 71/79; 71/118; 71/DIG. 1; 47/57.6
[58] Field of Search ...................... 71/77, 79, DIG. 1; 47/57.6

[56] References Cited

U.S. PATENT DOCUMENTS

| | | | |
|---|---|---|---|
| 4,124,748 | 11/1978 | Fujimoto et al. | 526/8 |
| 4,241,537 | 12/1980 | Wood | 47/77 |
| 4,552,938 | 11/1985 | Mikita et al. | 526/240 |
| 4,677,174 | 6/1987 | Alexander et al. | 526/240 |
| 4,906,276 | 3/1990 | Hughes | 71/77 |
| 7,525,527 | 6/1985 | Takeda et al. | 524/831 |

*Primary Examiner*—Glennon H. Hollrah
*Assistant Examiner*—Brian G. Bembenick
*Attorney, Agent, or Firm*—Marshall, O'Toole, Gerstein, Murray & Bicknell

[57] ABSTRACT

A method of improving the yield of crops utilizing an aqueous gel including a highly-absorbent, crosslinked, mixed salt of homopolymerized or copolymerized acrylic acid. The aqueous gels utilized in the present invention demonstrate improved crop yield even in the absence of plant nutrients.

7 Claims, No Drawings

METHOD OF IMPROVING CROP YIELD

CROSS REFERENCE TO RELATED APPLICATIONS

This is a continuation-in-part application to application Ser. No. 926,210 filed on Nov. 1986 now U.S. Pat. No. 4,906,276.

FIELD OF THE INVENTION

The present invention relates to a method of improving the crop yield of agricultural and horticultural plants. Improved crop yields are demonstrated for plants transplanted from a germination site, such as a greenhouse, to the field, and for plants germinated directly in the field. More particularly, the present invention relates to a method of improving the crop yield of agricultural and horticultural plants by utilizing an aqueous gel including a highly-absorbent, crosslinked, mixed salt of homopolymerized or copolymerized acrylic acid. The mixed salt of the polymerized acrylic acid forms an aqueous gel sufficiently strong to support the stem of a plant in the absence of inert solid aggregates, and, surprisingly, improves the crop yield of agricultural and horticultural plants in the absence of plant nutrients, growth promoters and other similar agricultural and horticultural adjuvants.

BACKGROUND OF THE INVENTION

Highly absorbent, crosslinked polymers have found wide use in a variety of applications, including sanitary goods, hygienic goods, water retaining agents, dehydrating agents, sludge coagulants, condensation preventing agents and release control agents for various chemicals. Water-absorbent polymers are available in a variety of chemical forms including substituted and unsubstituted natural and synthetic polymers such as hydrolysis products of starch-acrylonitrile graft polymers, carboxymethylcellulose, crosslinked polyacrylates, polyvinyl alcohols, polyacrylonitrile, polyvinylpyrrolidones, sulfonated polystyrenes, hydrolized polyacrylamides and polyethylene oxide.

In addition, aqueous gels, formed from the highly-absorbent crosslinked polymers of the present invention, have shown unexpected utility in increasing the crop yield of germinated plants. Such results are more surprising considering that it is not necessary to incorporate primary plant nutrients, micronutrients, growth promoters or other agricultural and/or horticultural adjuvants into the gel to increase the crop yields of germinated plants. Unexpectedly, it also has been found that aqueous gels including a mixed salt of homopolymerized or copolymerized acrylic acid generate higher crop yields when fertilizers are excluded from the aqueous gels.

It also has been found that it is unnecessary to admix inert solid aggregates, such as sand, rock, woodflour or vermiculite, with the mixed salt of the polymerized acrylic acid in order to help support a recently-germinated or a transplanted plant. The aqueous gels formed from the mixed salt polyacrylates of the present invention are of sufficient strength and rigidity to hold the plants upright, and also allow the roots of the germinated plant to withdraw the necessary water from the aqueous gel to preserve plant life.

Water-absorbent polymers have been used both to preserve freshly cut ornamental plants and as a growth medium for seeds, seedlings and transplants. U.S. Pat. No. 2,971,292 discloses a number of gel-forming colloidal materials, including polyacrylic polymers, that preserve the life of freshly cut plants. However, these gel-forming colloidal materials require the use of plant nutrients and the use of an inert solid aggregate filler to free water from the gel and thus make the water available for plant uptake. As will be seen in the detailed description of the invention, the inclusion of plant nutrients and inert solid aggregates into gels made from the polymers of the present invention is unnecessary, and is potentially detrimental.

Other patents disclosing the use of water absorbent polymers for use in plant preservation or as a plant growth medium include: U.S. Pat. No. 4,124,748, wherein a crosslinked copolymer of a vinyl ester and an unsaturated carboxylic acid ester, neutralized with a potassium or ammonium alkali, is suggested as a seed culturing media for plants; U.S. Pat. No. 4,241,537, wherein a nonionic, monolithic, crosslinked polyurethane is used as a soil plug for growing plants; U.S. Pat. No. 4,559,074, wherein a substantially nonionic crosslinked polyacrylamide is used as an additive for a plant growth medium; U.S. Pat. No. 4,238,374, wherein a water-insoluble crosslinked polymer and inert aggregate particles are utilized to preserve floral arrangements; U.S. Pat. No. 4,320,040, wherein a polyvinyl alcohol and polymerized acrylic acid composition is used as a water-retaining agent for plants or soils; and U.S. Pat. No. 3,336,129, wherein an absorbent crosslinked polymer and sand or soil are admixed to form plant growth modifiers. Several other U.S. Patents disclose polymers used in plant growth media, including U.S. Pat. Nos. 3,373,009; 3,900,378; 3,973,355; 4,034,508; 3,831,317; 4,495,310; 4,439,552; and 4,329,436.

The methods and compositions disclosed in the prior art require or recommend the inclusion of fertilizers and/or solid aggregates into the gels formed from the water-absorbent polymer. In addition, several of the prior art methods are difficult or impractical to use because: the compositions are not readily dispersed in water; the polymer, such as a starch-acrylonitrile graft polymer, is expensive and difficult to make; the polymer is subject to hydrolysis or bacterial degradation unless parameters, such as pH, are carefully controlled; the physical parameters, such as pH, necessary to protect the integrity of the polymer may adversely affect certain plants; and the polymers produce a gel that does not readily surrender water to the plants.

Therefore, it would be extremely advantageous to provide a method of increasing the crop yield of germinated plants by utilizing an aqueous gel including an economical, easy-to-synthesize, readily dispersible, non-degrading, water-absorbent polymer. It also would be advantageous if the polymer produced gels of sufficient gel strengths to support the stems of the plant without the need of inert solid aggregates, yet still be able to release the necessary water to the plant on demand. Finally, it would be most advantageous, both with respect to economy and ease of gel information, if aqueous gels formed from the polymer could be used without the addition of fertilizers and the like while providing nutrients to the plant.

Any method utilizing a polymer having the above-described qualities to increase crop yield would enhance and broaden the use of water-absorbent polymers in the agricultural and horticultural areas. Preferably, any such method should utilize an economical, easy-to-manufacture polymer that possesses qualities necessary to support plant life and improve crop yields, and that can be used at low percentages.

SUMMARY OF THE INVENTION

In brief, the present invention is directed to a method of improving crop yield of germinated plants by utilizing an aqueous gel including a highly-absorbent, crosslinked salt of a polyacrylate polymer. It has been found that the crop yields are increased by utilizing an aqueous gel of the polyacrylate salt in the absence of primary or secondary plant nutrients and/or in the absence of inert solid aggregates.

In accordance with the present invention, an aqueous gel, formed from a mixed salt of a highly-absorbent, crosslinked homopolymer or copolymer of acrylic acid, can improve the crop yield both of plants transplanted from a germination site, such as a greenhouse, to the field and of plants remaining at their original germination site. The method of the present invention has been found especially effective when an aqueous gel formed from the mixed salt of a crosslinked homopolymerized or copolymerized acrylic acid is used in the absence of an inert solid aggregate, a fertilizer or other plant nutrients.

Therefore, the present invention is directed to a method of improving the crop yields of agricultural and horizontal plants with an aqueous gel including a mixed salt of a water-absorbent, crosslinked homopolymer or copolymer of acrylic acid. The mixed salt of the polymers utilized in the present invention has unexpectedly and surprisingly shown increased crop yield for agricultural and horticultural plants when compared to similar non-mixed salts of polyacrylic acid, and when compared to other crosslinked water-absorbant polymers, such as hydrolyzed starch-acrylonitrile graft polymers.

More particularly, the present invention is directed to a method of improving the crop yields of agricultural and horticultural plants and by utilizing an aqueous gel including a homopolymer or copolymer of acrylic acid that is neutralized with both potassium and ammonium alkalis. Compared to polymers of similar chemical structure, and to polymers of a different chemical structure, the polymers used in the method of the present invention have shown a superior ability to increase crop yield and promote plant life. Without being limited to any particular mechanism, it is theorized that such improvements in crop yield are due to the method of manufacture of the polymer wherein a heated aqueous solution comprising (A) acrylic acid neutralized 70 to 100 mole percent with ammonium and potassium alkalis; and (B) a water-miscible to water-soluble polyvinyl monomer, and water and having a combined monomer concentration of (A) plus (B) of 30 to 80 wt. % is subjected to polymerization in the presence of a polymerization initiator without external heating while allowing water to evaporate during polymerization. Takeda et al U.S. Pat. No. 4,525,527 and Mikita et al. U.S. Pat. No. 4,552,938 disclose methods for making similar polymers without the step of external heating.

Similarly, copolymers that are useful in the method of the present invention are synthesized by an aqueous polymerization of (A) acrylic acid neutralized 70 to 100 mole percent with ammonium, and potassium alkalis; with (B) styrene an amount of 1% to 25% based on the weight of acrylic acid or acrylate, computed as based on acrylic acid; and (C) a water-miscible or a water-soluble polyvinyl monomer in an amount of 0.001 to 0.3 weight percent based on the total weight of (A), (B) and (C).

Therefore, it is an object of the present invention to provide a method of increasing the crop yield of agriculatural and horticultural plants. It is also an object of the present invention to provide a method of increasing the crop yield of horticultural and agricultural plants by utilizing an aqueous gel including a highly-absorbent, crosslinked polymer.

Another object of the present invention is to provide a method of increasing the crop yield of agricultural and horticultural plants by utilizing an aqueous gel including a mixed salt of a crosslinked, homopolymerized or copolymerized acrylic acid.

Another object of the present invention is to provide a method of increasing the crop yield of agricultural and horticultural plants by utilizing a homopolymerized or copolymerized acrylic acid neutralized with both potassium and ammonium alkalis.

Another object of the present invention is to provide a method of increasing the yield of agricultural and horticultural plants by synthesizing potassium and ammonium-neutralized, homopolymers and copolymers of acrylic acid that are suitable for supplying the crops and plants with the required water and nutrients for their continued growth and life.

Still another object of the present invention is to provide a method of increasing the crop yield of agricultural and horticultural plants by utilizing an aqueous gel including the mixed potassium and ammonium salt of a homopolymer or copolymer of acrylic acid, in the absence of plant nutrients, inert solid aggregates or agricultural or horticultural adjuvants.

These and other objects and advantages of the present invention will become apparent from the following detailed description of the invention.

DETAILED DESCRIPTION OF THE INVENTION

In accordance with the present invention, an aqueous gel, formed from a highly absorbent, crosslinked polymer, unexpectedly and surprisingly improves the crop yield of agricultural and horticultural plants. As will be discussed more fully hereinafter, the polymers used in the method of the present invention are mixed potassium and ammonium salts of a homopolymer or copolymer of acrylic acid. These polymers form aqueous gels that exhibit substantial increases in crop yields of agricultural and horticultural plants in comparison to aqueous gels obtained from chemically similar, and from chemically different, polymers. Quite surprisingly, the polymers of the present invention exhibit a greater improvement in crop yields when fertilizers and other agricultural or horticultural adjuvants are absent from the gel.

Also, aqueous gels formed from the mixed salt polymers of acrylic acid are of sufficient strength to support the roots and the stem of the plant even in the absence of inert solid aggregates. In addition, the polymers used in the method of the present invention possess sufficient water-absorbing and swelling ability such that suitable gels are formed using very low percentages of polymers, therefore providing a sufficient amount of free, unbound water to the plant for uptake upon demand.

In addition to clays and natural gums, several types of water-absorbing crosslinked polymers have been used to form aqueous gels that are useful as a plant growth medium or plant preservation medium. However, the previous methods and compositions all possess disadvantages that severely limit their practical utility. For instance, gels made from clays are often difficult and messy to prepare; polymers based on natural gums or natural polymers, such as starch, are subject to chemical and bacterial degradation; some polymers must be used in a high percentage and may bind the water to such a degree that sufficient water is not available for use by the plant; polymers incapable of surrendering the water from the gel to the plant must be combined with inert solid aggregates in order to free some water for use by the plant; and some of the polymers utilized to make the gels are expensive and difficult to prepare.

As will become apparent from the following detailed description of the invention, the method of the present invention utilizes polymers that are easy and economical to synthesize, resist degradation and possess the requisite physical characteristics, such as gel strength, fast water-absorption and dispersibility, that make them ideal for use in plant growth media. The method of the present invention utilizes polymers that are non-toxic to plants; are sufficiently crosslinked to be water-insoluble, yet are able to absorb water and swell and disperse in water; are effective at low percentages; form transparent gels; easily release absorbed-water from the gel to materials having a lower concentration of water than the gel; and are sufficiently inert such that the composition of the gel can include other common additives without adversely affecting the basic utility of the polymer.

The polymers that have found particular utility in the method of the present invention include the mixed salts of homopolymerized or copolymerized acrylic acid. More particularly, the potassium and ammonium mixed salts of polyacrylic acid, or the potassium and ammonium mixed salts of copolymers of acrylic acid and styrene can be used to form aqueous gels that increase the crop yield of germinated plants. However, to achieve the full advantage of the present invention, a polyacrylic acid, neutralized both with a potassium alkali and an ammonium alkali, is used to form an aqueous gel for improving crop yields.

As will be more fully discussed hereinafter, according to the method of the present invention, an aqueous gel formed from the potassium and ammonium mixed salt of polyacrylic acid, or from the potassium and ammonium mixed salt of acrylic acid copolymerized with styrene surprisingly and unexpectedly increases the crop yields of agricultural and horticultural plants in comparison to gels formed both from chemically similar polymers and chemically dissimilar polymers. The polymers used in the method of the present invention are synthesized from a monomer mix including ammonium acrylate and potassium acrylate, theoretically accounting for the improved results over acrylic acid polymers that are neutralized after polymerization. Preneutralization of the monomer mix assures not only a more complete neutralization, but also a more random and even distribution of the ammonium and potassium ions along the polymer chain.

More particularly, polymers that can be used in the method of the present invention are synthesized by first preparing a hot aqueous solution comprised of acrylic acid neutralized 70 to 100 mole percent, a water-miscible or water-soluble polyvinyl monomer, water and, when desired, an organic solvent having a boiling point of 40° to 150° C., wherein the acrylate monomer and the polyvinyl monomer are present in a combined concentration of 30 to 80 wt. %. To achieve the full advantage of the present invention, the acrylate and polyvinyl monomers are present in a combined concentration of less than 70 weight percent of the monomer solution.

In accordance with another important embodiment of the present invention, the combined concentration of the acrylate and polyvinyl monomers is less than 55 weight percent of the monomer solution. The concentration of the monomers is deliberately determined considering the state of the solution (i.e., as to whether or not the monomers can be completely dissolved in water), ease of the reaction of the monomers, escape of the monomers due to the scattering during the reaction, and the like. The aqueous solution can be prepared easily by placing the acrylic acid, the strong potassium and ammonium alkalis, e.g. potassium hydroxide and ammonium hydroxide, for neutralizing the acid and the polyvinyl monomer into water in such amounts that the resulting solution has the abovementioned monomer concentration. In accordance with one important embodiment of the present invention, the ratio of potassium ions to ammonium ions should range from approximately 70:30 to 30:70. To achieve the full advantage of the present invention the ratio of potassium ion to ammonium ions should range from approximately 55:45 to 45:55. To dissolve the monomers thoroughly, the mixture can be heated to an elevated temperature.

Although it is desirable to use the neutralizing agent usually in an amount sufficient to neutralize acrylic acid 100 mole %, there is no particular need to neutralize the acid 100% insofar as the neutralizing agents are used in such an amount as to achieve not less than about 70% neutralization. However, too large a quantity of free acrylic acid, if present in the aqueous solution, is likely to partly splash out of the reaction vessel, resulting in a loss during the reaction, leading to a reduced degree of polymerization. The use of an excessive amount of the neutralizing agent will not raise any particular problem, but the excess does not participate in the polymerization reaction and is therefore useless and wasted.

In accordance with another important embodiment of the present invention, acrylic acid neutralized 70–100 mole percent is mixed with 1% to 25%, based on the weight of acrylic acid, styrene and a water-miscible or water-soluble polyvinyl monomer in an aqueous solution at a temperature of about 20° to 100° C. The solution is subjected to a polymerization reaction and a crosslinking reaction by the addition of a polymerization initiator. The polymerization reaction proceeds sufficiently within a very short period of time and if the monomer concentration is at least 30 percent by weight of the aqueous monomer mixture, the heat of the copolymerization and crosslinking reactions will evaporate water rapidly from the reaction system to form a dry solid (less than 15 percent by weight water), water-absorbing resin without the need for any subsequent drying step. The solid can be easily pulverized into a powder suitable for the desired use.

The polyvinyl monomer used to crosslink the polymers of the present invention should be miscible with, or soluble in, water so that the monomers are uniformly dissolved or dispersed in the aqueous solution of the monomer mixture. Examples of such polyvinyl monomers include bisacrylamides such as N,N'-methylenebisacrylamide and N,N'-methylenebismethacrylamide; polyacrylic (or polymethacrylic) acid esters represented by the following formula (I); and diacrylamides represented by the following formula (II). Among these, especially preferably are N,N'-methylenebisacrylamide, N,N'-methylenebismethacrylamide and like bisacrylamides.

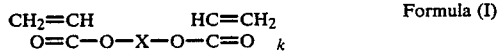
Formula (I)

wherein X is ethylene, propylene, trimethylene, hexamethylene, 2-hydroxypropylene, $(CH_2CH_2O)_nCH_2CH_2$— or

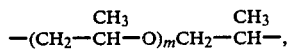

of from 5 to 40, and k is 1 or 2.

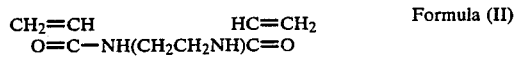
Formula (II)

wherein is 2 or 3.

The polyvinyl monomer is used in an amount of about 0.001 to 0.3 wt. % of the combined amount of acrylic acid and styrene monomers in the aqueous monomer mixture. In accordance with another important embodiment of the present invention, the polyvinyl monomer cross-linking agent should be present in the aqueous solution in an amount of at least 0.2 wt. % based on the total weight of monomers to provide a resin sufficiently cross-linked to avoid water solubility. If the polyvinyl monomer is included in the aqueous solution in an amount of 0.2 to 0.6 weight percent based on the weight of neutralized acrylic acid and polyvinyl monomers, the resulting polymer will have a sufficient degree of crosslinking to avoid solubilization on absorption of water.

The aqueous mixed monomer solution is heated and thereafter subjected to polymerization or copolymerization and cross-linking reactions with the addition of a polymerization initiator. Although the temperature of the aqueous mixed monomer solution is not particularly limited since the mixed monomer solution is initiated into polymerization by the addition of the initiator, the temperature is usually about 50° C. to about 85° C., preferably about 60° C. to about 75° C.

Various polymerization initiators are usable that are known for use in preparing polyacrylates. Examples of useful initiators are redox initiators comprising a reducing agent, such as a sulfite or bisulfite of an alkali metal, ammonium sulfite or ammonium bisulfite, and an initiator, such as a persulfate of an alkali metal or ammonium persulfate, in combination with the reducing agent; azo initiators including azobisisobutyronitrile, 4-t-butylazo-4'-cyanovaleric acid, 4,4'-azobis(4-cyanovaleric acid) and 2,2'-azobis(2-amidinopropane) hydrochloride; and the like. These initiators can be used singly or in a suitable combination. Of these, especially preferable are a redox initiator composed of ammonium persulfate and sodium hydrogen sulfite, and azo initiators such as azobisisobutyronitrile and 2,2'-azobis(2-amidinopropane)-hydrochloride. The initiators are advantageously used usually in the form of an aqueous solution but can be used as diluted with a suitable solvent. The initiator is used in a usual amount, i.e., in an amount, calculated as solids, of about 0.1% to about 10%, preferably about 0.5% to about 5%, of the combined weight of the monomers, namely acrylate (and free acrylic acid); styrene (if any); and polyvinyl monomer cross-linking agent. Depending on the amount and kind of the initiator, the initiator can be used together with isopropyl alcohol, an alkylmercaptan or other chain transfer agents to control the molecular weight of the polyacrylate copolymer to be obtained.

The following Examples are illustrative of the polymers that can be utilized in the method of the present invention.

EXAMPLE 1

To deionized water in a storage vessel is added, wherein percents are weight percents based on the total weight of the monomer solution formed, 58.81% acrylic acid first, then 11.76% potassium hydroxide and 11.76% ammonium carbonate and 14.70% ammonium hydroxide serving as neutralizing agents. Thereafter 0.03% of N, N-methylenebisacrylamide as a polyvinyl monomer is added to prepare an aqueous solution of potassium acrylate and ammonium acrylate in 2.79% of water having a neutralization degree of about 90% and a combined monomer concentration of 58.84 wt. %. The monomer solution is held in a storage vessel until the polymer solution process begins by feeding polymerization initiator from a second storage vessel simultaneously with monomer solution from the first storage vessel into the reaction vessel.

The aqueous solution is maintained at 70° C., and with the solution in the reaction vessel is continuously admixed to maintain a concentration of 0.15% of 2,2-azobis(2-amidino-propane)hydrochloride. The final solution is as follows:

| CHEMICALS | PERCENT |
| --- | --- |
| ACRYLIC ACID | 58.81% |
| POTASSIUM HYDROXIDE | 11.76% |
| AMMONIUM CARBONATE | 11.76% |
| N,N-METHYLENEBISACRYLAMIDE | 0.03% |
| POLYMERIZATION INITIATOR | 0.15% |
| AMMONIUM HYDROXIDE (30% aqueous ammonia) | 14.70% |
| WATER | 2.79% |
| TOTAL | 100.00 |

The polymer is allows to complete curing for about 30 minutes at ambient temperature to give a dry, solid mass of a crosslinked potassium and ammonium polyacrylate producing having a water content of 11% and a residual monomer concentration of 1200 ppm. The resin is made into a powder by a pulverizer.

EXAMPLE 2

The following mixed monomer solution was reacted in the same manner as described in Example 1 to give a dry, solid mass of crosslinked potassium/ammonium polyacrylate.

| CHEMICALS | PARTS BY WEIGHT | PERCENT |
| --- | --- | --- |
| ACRYLIC ACID | 16.80 | 54.15% |
| AMMONIUM HYDROXIDE (30% aqueous ammonia) | 4.20 | 13.54% |
| POTASSIUM HYDROXIDE | 4.20 | 13.54% |
| AZO INITIATOR | 0.13 | 0.42% |
| GPTA (glycerol propoxy triacrylate molecular weight 428.5) | 0.002 | 0.01% |
| AMMONIUM CARBONATE | 3.31 | 10.67% |

| CHEMICALS | PARTS BY WEIGHT | PERCENT |
|---|---|---|
| WATER | 2.30 | 7.67% |
| TOTAL | 30.94 | 100.00% |

EXAMPLE 3

| CHEMICAL | PARTS BY WEIGHT | PERCENT |
|---|---|---|
| ACRYLIC ACID | 16.80 | 53.57% |
| AMMONIUM HYDROXIDE (30% aqueous ammonia) | 4.20 | 13.39% |
| POTASSIUM HYDROXIDE | 4.20 | 13.39% |
| STYRENE | 0.81 | 1.08% |
| AZO INITIATOR | 0.13 | 0.42% |
| GPTA (glycerol propoxytriacrylate molecular weight 428.5) | 0.002 | 0.01% |
| AMMONIUM CARBONATE | 3.31 | 10.55% |
| WATER | 2.38 | 7.59% |
| TOTAL | 31.83 | 100.00% |

EXAMPLE 4

| CHEMICALS | PERCENT |
|---|---|
| ACRYLIC ACID | 58.23% |
| STYRENE | 1.58% |
| POTASSIUM HYDROXIDE | 11.76% |
| AMMONIUM CARBONATE | 11.76% |
| N,N-METHYLENEBISACRYLAMIDE | 0.03% |
| AZO INITIATOR | 0.15% |
| AMMONIUM HYDROXIDE (30% aqueous ammonia) | 14.70% |
| WATER | 1.79% |
| TOTAL | 100.00% |

The mixture is poured onto a traveling end-less belt and spread thereover in the form of a layer about 10 mm in thickness. About 30 seconds thereafter, the mixture starts to polymerize, and the reaction is completed in about 1 minute. The maximum temperature of the mixture during the reaction is about 120° C.

The copolymer is allowed to complete curing for about 30 minutes at ambient temperature to give a dry solid strip of potassium/ammonium polyacrylatepolystyrene product having a water content of 11% and a residual monomer concentration of 1200 ppm. The strip is made into a powder by a pulverizer.

EXAMPLE 5

The following mixed monomer solution was reacted in the same manner as described in Example 4 to give a dry solid strip of potassium/ammonium polyacrylate-polystyrene product of low water content and low residual monomer concentration.

| CHEMICALS | PERCENT |
|---|---|
| ACRYLIC ACID | 56.01% |
| STYRENE | 2.80% |
| POTASSIUM HYDROXIDE | 11.76% |
| AMMONIUM CARBONATE | 11.76% |
| N,N-METHYLENEBISACRYLAMIDE | 0.03% |
| AZO INITIATOR | 0.15% |
| AMMONIUM HYDROXIDE (30% aqueous ammonia) | 14.70% |
| WATER | 2.79% |
| TOTAL | 100.00% |

To demonstrate the new and unexpected results achieved by the mixed salt polyacrylates of the present invention, a highly-absorbent, crosslinked polymer, synthesized according to the method of Example 1, was tested for its ability to support freshly cut flowers. An aqueous gel, made by dispersing approximately 0.1% by weight of the crosslinked, insoluble mixed potassium-/ammonium polyacrylate synthesized according to the method of Example 1 in tap water, was tested for its ability to support freshly cut roses. It was found that this low percentage of polymer generated gels of sufficient consistency and gel strength to support the flower stems in an upright position. In these tests, water is first added to a vase, then the mixed salt polyacrylate is added slowly to the water and dispersed. It is not necessary, or desirable, to use hot water to disperse to polymer. The dispersion process is not a dissolving process, but a physical water-absorption and polymer-swelling process, wherein the polymer absorbs many times its weight in water and swells many times its volume. The use of hot water may adversely affect the plants inserted into the gel. Within a few minutes of its addition to the water, the mixed salt polyacrylate has absorbed sufficient water to swell and form a gel of the desired gel strength. Freshly-cut roses were inserted into the gel and were vertically supported without the need to add inert solid aggregates.

Prior art methods require a relatively large amount of polymer to generate a gel of sufficient consistency and strength to support plant stems. The prior art also teaches that increasing the percentage of polymer in the gel reduces the ability of the gel to give up water to the plant as the plant requires. For instance, in U.S. Pat. No. 4,238,374, increasing the amount of a monovalent salt of polyacrylic acid to coat the inert solid aggregate of the mixture resulted in the flowers dying four days earlier than in gels utilizing a lower percentage of polymer. This result has been attributed to a gel thickness that is too great for water uptake by the plants. Therefore, an important feature in the method of the present invention is the low percentage, of from about 0.4% to about 0.7% by weight, of the potassium/ammonium acrylate polymer that is necessary to obtain the unexpected crop yield improvements.

Consequently, an important feature of the method of the present invention is the ability of the potassium/ammonium polyacrylate polymer to easily give up its absorbed water to the plant upon demand. Several prior art polymers generate gels of sufficient strength and consistency to support plant stems. However, the absorbed water is held by the polymer so tightly that the water is not available to the plant. Therefore, inert solid aggregates are included to free some water from the polymer for use by the plants. Surprisingly, the polymers of the present invention are able to supply the agricultural and horticultural plants with water that the plants require, without the addition of a solid inert aggregate. Furthermore, the polymers used in the method of the present invention include nitrogen and potassium plant nutrients incorporated into the polymeric structure. Surprisingly, these plant nutrients are available to the plant when the agricultural and horticultural plant requires them.

To further demonstrate the new and unexpected results achieved by the method of the present invention, aqueous gels made from the mixed ammonium/potassium salts of the polyacrylates of the present invention were shown to increase the crop yield of agricultural and horticultural plants and decrease losses in germinated seedlings. For example, Tables I and II illustrate the effect of using an aqueous gel including a mixed potassium/ammonium salt of a polyacrylate of the present invention in the transplanting starter solution on the yield of Yolo Wonder L Peppers.

EXAMPLES 6-17

Ten week old pepper transplants were planted in a field, in rows 6.1 meters long with 0.9 meters between the rows. The plants were spaced 0.4 meters apart. Each plant received 200 ml. of starter solution and/or gel solution, applied to the roots in the planting hole. The hole was then covered with soil. Marketable yields were recorded after approximately 10 weeks, 13 weeks and 16 weeks after transplanting. The values in Table II for the pepper yields are the average of three replications. Table I lists the amount of polymer and/or starter fertilizer used in each example. Gels containing polymer and fertilizer (EX. 13 through 17) required a higher percentage of polymer in order to maintain similar gel viscosities.

TABLE I

| EXAMPLES | TREATMENT | CONCENTRATION |
|---|---|---|
| 6 | Untreated | — |
| 7 | 12-48-8 (SOL-U-GRO)[1] | 0.72% (wt/v) |
| 8 | TERRA-SORB GB[2] | 0.60% (wt/v) |
| 9 | SUPRASORB-1000[3] | 0.60% (wt/v) |
| 10 | A.C. POLYMER | 0.60% (wt/v) |
| 11 | ABG-7005[4] | 0.41% (wt/v) |
| 12 | LIQUA-GEL[5] | 0.60% (wt/v) |
| 13 | TERRA-SORB GB + 12-48-8 | 1.30% + 0.72% (wt/v) |
| 14 | SUPRASORB-1000 + 12-48-8 | 1.00% + 0.72% (wt/v) |
| 15 | A.C. POLYMER + 12-48-8 | 1.50% + 0.72% (wt/v) |
| 16 | ABG-7005 + 12-48-8 | 1.04% + 0.72% (wt/v) |
| 17 | LIQUA-GEL + 12-48-8 | 1.20% + 0.72% (wt/v) |

[1] SOL-U-GRO is a starter fertilizer solution containing 12% by weight nitrogen as N; 48% by weight phosphorus by weight as $P_2O_5$ and 8% potassium by weight as $K_2O$.
[2] TERRA-SORB GB is a crosslinked, waterswellable acrylamide-potassium acrylate copolymer and available commercially from Industrial Services International, Inc., Bradenton, Florida.
[3] SUPRASORB-1000 is a starch-acrylonitrile graft polymer hydrolyzed with sodium hydroxide and available commercially from Super Absorbent Industries, Lumberton, SC.
[4] ABG-7005 is a starch-acrylonitrile graft polymer hydrolyzed with potassium hydroxide and available commercially from Abbott Laboratories, North Chicago, IL.
[5] LIQUA-GEL is a starch acrylonitrile graft copolymer and available commercially from Miller Chemical and Fertilizer Corp., Hanover, PA.

As set forth in Table II, Examples 7 through 17 are compared to the untreated control Example 6. Example 7 contains only a fertilizer solution, whereas Examples 8, 9, 11 and 12 are aqueous gels, each containing only a competitive crosslinked water-swellable polymer. The competitive polyacrylate polymer of Example 8 is synthesized via an inverse polymerization process in a water-hydrocarbon solution. In the inverse polymerization process, the water-hydrocarbon solution is evaporated after polymerization, then the polymer is dried, and finally the polymer is ground to an appropriate size before use. The process of manufacture of these polyacrylate polymers is appreciably different from the method of manufacture of the polymers used in the present invention, theoretically accounting for the inferior results of these chemically-similar polymers when compared to the polymers utilized in the present invention.

The aqueous gel of Example 10 is formed from the mixed potassium/ammonium polyacrylate synthesized according to the method outlined in Example 1, and the aqueous gel of Example 15 is formed from the same potassium/ammonium polyacrylate in conjunction with the fertilizer solution of Example 7. The aqueous gels of Examples 13, 14, 16 and 17 are formed from competitive crosslinked polymers in conjunction with the starter fertilizer of Example 7. Table II illustrates the effect of the solutions and gels of Examples 6 through 17 on the yield of Yolo Wonder L Peppers.

TABLE II

Effect of Gels on the Yield of Yolo Wonder L Peppers

| EXAMPLE NUMBER | TOTAL NUMBER OF FRUIT | TOTAL WT. FRUIT (Kg) | WT. FRUIT PER PLANT (Kg) |
|---|---|---|---|
| 6 | 90.33 | 13.30 | 1.00 |
| 7 | 97.67 | 13.97 | 1.03 |
| 8 | 100.67 | 13.46 | 1.01 |
| 9 | 68.00 | 8.41 | 0.59 |
| 10 | 132.00 | 18.24 | 1.27 |
| 11 | 104.67 | 13.76 | 0.92 |
| 12 | 113.67 | 16.80 | 1.12 |
| 13 | 106.00 | 14.73 | 1.00 |
| 14 | 62.00 | 8.07 | 0.69 |
| 15 | 111.00 | 15.39 | 1.13 |
| 16 | 112.00 | 15.37 | 1.06 |
| 17 | 117.67 | 16.32 | 1.19 |

It is most surprising and unexpected that aqueous gels made from the mixed potassium/ammonium salt of crosslinked polyacrylic acid (Example 10) not only demonstrate improved yields in total number of fruit, total weight of fruit, and the weight of fruit per plant compared to the untreated control (Example 6), but all three yield measurements also are improved when compared to using starter fertilizer alone (Example 7), and when compared to an aqueous gel including starter fertilizer and the mixed potassium/ammonium salt of crosslinked polyacrylic acid (Example 15). The aqueous gel containing the mixed potassium/ammonium salt of crosslinked polyacryl acid (Example 10) of the present invention also shows improved yields over each of the competitive polymers, both when the competitive product is used alone and the competitive product is used in conjunction with the starter fertilizer.

To illustrate, Example 10, utilizing an aqueous gel containing only the potassium/ammonium polyacrylate synthesized according to the method of Example 1, shows a 46% increase in the total number of fruit, a 37% increase in the total weight of fruit, and a 27% increase in the weight of fruit per plant over the untreated control of Example 6. Likewise, Example 10 shows respective yield increases of 35%, 30% and 23% over Example 7, that utilizes a transplanting fertilizer solution. It is completely unexpected for the mixed ammonium/potassium polyacrylate salts used in accordance with the present invention to outperform transplant fertilizer solutions. Surprisingly, the assumed and expected further yield improvements from adding a fertilizer to an aqueous gel formed from the mixed ammonium/potassium polyacrylate salt is not observed. As seen in Example 15, this combination exhibits yields that are improved over the use of fertilizers alone (Example 7), but gives yields that are well below those obtained using an aqueous gel including the mixed ammonium/potassium polyacrylate salt but absent fertilizer (Example 10).

In every case, the mixed ammonium/potassium polyacrylate salt (Example 10) used in the method of the present invention gave improved yields over the competitive gel-forming polymers of Examples 8, 9, 11 and 12. Yield results from tests using competitive polymers to form the aqueous gel ranged from 20% to 70% lower in total number of fruit, 11% to 73% lower in total weight of fruit, and 15% to 96% lower in weight of fruit per plant compared to the yield results of Example 10. In tests utilizing an aqueous gel formed from combining a competitive polymer with a fertilizer, some examples exhibited improved yields compared to the aqueous gels using the competitive polymer alone, and some examples exhibited decreased yields compared to aqueous gels using the competitive polymer alone, however, in none of the tests were the yields improved to a greater degree than the increases observed in using the mixed ammonium/potassium polyacrylate salts (Example 10).

To further demonstrate the new and unexpected results achieved by the method of the present invention, aqueous gels prepared from the mixed ammonium/potassium salts of the polyacrylates of the present invention were allowed to contact the root area of transplanted Heinz 1350 tomatoes seedlings and transplanted Honeymoon sweet corn seedlings. The crop yields harvested from the tomato plants and the sweet corn plants that contacted the water-absorbent polyacrylate of the present invention then were compared to the crop yield of tomatoes and sweet corn harvested from tomato plants and sweet corn plants that were not treated with water-absorbent crosslinked polyacrylic polymers of the present invention.

In order to demonstrate the new and unexpected results achieved by the method of the present invention, an aqueous gel comprising 0.6% w/v of the mixed ammonium/potassium polyacrylate salt of the present invention, i.e., a polymer, synthesized according to the method of Example 1, and designated as A.C. Polymer, was applied to the root area of transplanted Heinz 1350 tomato seedlings and to the root area of transplanted Honeymoon sweet corn seedlings as a fluid sowing gel to show the ability of the gel to increase the crop yield of tomato and sweet corn plants with respect to total number of emerged plants, length of time for plant emergence, and amount of harvested crop.

In the experiments performed on the Heinz 1350 tomato plants, the root area of each tomato seedling on one test plot was treated with 200 ml of a fluid sowing gel including 0.6% w/v (weight/volume) of an aqueous gel of the polymer of the present invention. A second test plot of Heinz 1350 tomato seedlings was not treated with an aqueous gel of the polymer of the present invention. At harvest, the tomato plant crops on the two test plots were compared in regard to the total number of tomato plants at harvest and the amount of red tomatoes harvested as a percent of the total crop yield of the Heinz 1350 tomatoes, i.e. the percent of marketable tomato crop. The harvest yields are presented in TABLE III, illustrating the effect of contacting the root area of Heinz 1350 tomato plant seedlings with an aqueous gel of A.C. Polymer on the yield of Heinz 1350 tomatoes. As set forth in TABLE III, Heinz 1350 tomato seedlings treated with an aqueous gel of the A.C. Polymer surprisingly and unexpectedly showed a 20% increase in total number of tomato plants at harvest, and a 39.5% increase in marketable red fruit.

TABLE III

Effect of Gels on the Yield of Heinz 1350 Tomatoes

| EXAMPLE NUMBER | TREATMENT | CONC. | NO. PLANTS AT HARVEST | % RED TOMATOES (as % of total amount of harvested fruit) |
|---|---|---|---|---|
| 18 | Untreated | 0 | 38 | 19.48% |
| 19 | A.C. Polymer | 0.6% (w/v) | 45.6 | 26.0% |

In the experiment performed on Honeymoon sweet corn, the root area of Honeymoon sweet corn seedlings on one test plot was treated with 200 ml. of a fluid sowing gel including 0.6% w/v of an aqueous gel of the A.C. Polymer. A second test plot of transplanted Honeymoon sweet corn seedlings was not treated with the aqueous gel. At harvest, the sweet corn plants on the two plots were compared in regard to the number of days to attain 50% plant emergence (i.e., the number of days wherein one-half of the total number of emerged plants emerged); the total number of emerged sweet corn plants; and the total number of days for final emergence of the sweet corn plants. The data is summarized in TABLE IV, illustrating the effect of contacting the root area of transplanted Honeymoon sweet corn seedlings with an aqueous gel of A.C. Polymer on the yield of Honeymoon sweet corn. As set forth in TABLE IV, Honeymoon sweet corn seedlings treated with an aqueous gel of the A.C. Polymer surprisingly and unexpectedly reduced the amount of time for 50% of the sweet corn plants to emerge by 17%; reduced the amount of time for total emergence of the sweet corn plants to emerge by 25%; and increased the total number of emerged sweet corn plants by 19.3%.

TABLE IV

Effect of Gels on the Yield of Honeymoon Sweet Corn

| EXAMPLE NUMBER | TREATMENT | CONC. | NO. OF DAYS FOR 50% EMERGENCE | NO. OF DAYS FOR TOTAL EMERGENCE | NO. OF PLANTS AT TOTAL EMERGENCE |
|---|---|---|---|---|---|
| 20 | Untreated | 0 | 8.64 | 13.5 | 17.6 |
| 21 | A.C. Polymer | 0.6% (w/v) | 7.36 | 10.8 | 21.0 |

Accordingly, for both Heinz 1350 tomatoes and Honeymoon sweet corn, test plots including the mixed ammonium/potassium polyacrylate salt, i.e., the A.C. Polymer manufactured according to the method of Example 1, provided improved crop yields (i.e., EX. 8 and 20) over test plots not including the A.C. Polymer (i.e., EX. 19 and 21). As previously described, crop yield data from experiments performed on transplanted Yolo Wonder L pepper plants treated with aqueous gels of the A.C. Polymer showed similar increases in crop yield. Therefore, the data presented in TABLE III, relating to crop yield improvements in Heinz 1350 tomato crops, and in TABLE IV relating to crop yield improvements in Honeymoon sweet corn crops, in addition to the crop yield improvements in Yolo Wonder L peppers as presented in TABLE II, demonstrate that applying an aqueous gel including the mixed potassium/ammonium salt of crosslinked polyacrylic acid of the present invention to the root area of a transplanted crop unexpectedly improves the crop yield in total number of fruit, total weight of fruit, weight of fruit per plant, and time required for plant emergence for a variety of crops.

Furthermore, the method of the present invention is not limited to improving the crop yield of only transplanted germinated crops. In accordance with an important feature of the present invention, improved crop yields are envisioned provided the aqueous gel of the mixed salt polyacrylate contacts the root area of the treated plant. In addition to transplanting the germinated plant to allow contact between the aqueous gel and the root area of the plant, several other methods of treating the germinated plant are available. For example, after a plant seed has germinated, the soil immediately surrounding the root area of the plant can be removed and the aqueous gel then is added to the root area of the plant to allow contact between the aqueous gel and root area of the plant. The soil then can be replaced to cover the root area of the plant. Alternatively, the germinated plant can be removed from its germination site, the aqueous gel is added to the void resulting from removing the plant from the soil, then the germinated plant is replaced into its original germination site. Therefore, overall, the root area of the plant can be contacted with an aqueous gel comprising from about 0.4% to about 0.7% by weight of a mixed potassium and ammonium salt of a crosslinked polyacrylate, without the need to transplant the plant.

Furthermore, it also is envisioned that the aqueous gel can be placed in a position sufficiently close to a planted seed, or in a position contacting a planted seed, such that after seed germination, the aqueous gel already is present in the plant growth medium for essentially immediate contact with the roots of the plant. It has been found that direct contact of a plant seed with the aqueous gel of the present invention did not adversely affect the germination of the plant seed. Therefore the aqueous gel can be positioned in the soil concurrently, and in contact, with the plant seed to provide an improved crop yield of an agricultural or a horticultural plant.

As previously stated, the mixed polyacrylate salt of the present invention has nitrogen and potassium available for use by the agricultural or horticultural plant or seedling. In addition, the mixed salt polyacrylates of the present invention have the ability to release water to the plant upon demand because the polymer does not bind the water to such an extent that the water in the aqueous gel is unavailable to plant. Such a result is surprising and unexpected for polymers that have such high water-retention capacities. It is a particular and distinct advantage of the mixed ammonium/potassium polyacrylate salts of the present invention that they have the ability to retain large amounts of water and that they also have the ability to surrender that water to the plant on demand. These unique capabilities thereby reduce moisture stress on the plants during dry or drought periods. The polymers useful in the method of the present invention are capable of preferentially absorbing the water in relation to soil, and will hold this moisture for release to the roots contacting the polymer upon demand. Consequently, by reducing the stress effects resulting from a lack of moisture, more seeds and seedlings germinate and emerge from the soil and crop yields are directly increased.

The method of the present invention also can be used to improve the crop yields of any other cash crop such as sweet corn, brussels sprouts, beans, tomatoes and strawberries, or to reduce the number of lost transplants in plants such as tobacco, annuals and perennials, woody plants and ornamentals.

It should be understood that the present disclosure has been made only by way of preferred embodiment and that numerous changes in details of construction, combination and arrangement of parts can be resorted to without departing from the spirit and scope of the invention as hereunder claims.

What is claimed and sought to be secured by Letters Patent of the United States is:

1. A method of increasing the yield of crops comprising contacting a plant root with an aqueous gel comprising from about 0.4% to about 0.7% by weight of a mixed potassium and ammonium salt of a crosslinked, copolymerized or homopolymerized acrylate and covering the plant root and the aqueous gel with soil; wherein the mixed potassium and ammonium salt of a crosslinked, copolymerized or homopolymerized acrylate is prepared by mixing a monomer-solution of (A) acrylic acid neutralized 70 100 mole percent with a potassium alkali and an ammonium alkali; (B) styrene in an amount of 0% to 25% based on the weight of acrylic acid and (C) a water-miscible to water-soluble polyvinyl monomer in a combined concentration of (A), (B) and (C) of at least 30 wt. %; with water to form a mixed monomer-solution and initiating polymerization of monomers (A), (B) and (C) such that during polymerization, the exothermic heat of reaction is substantially the only heat energy used to accomplish polymerization, cross linking and to drive off sufficient water to obtain a solid crosslinked resin having a water content of 15 percent by weight or less.

2. The method of claim 1 wherein the combined concentration of the monomers (A), (B) and (C) is at least 30 wt. % and less than 70 wt. %.

3. The method of claim 1 wherein monomer (C) is selected from the group consisting of N,N methylenebisacrylamide and N,Nmethylenebismethacrylamide.

4. The method of claim 1 wherein the potassium alkali and the ammonium alkali are selected from the group consisting of potassium hydroxide, potassium carbonate, potassium bicarbonate, ammonia, ammonium hydroxide, ammonium carbonate and ammonium bicarbonate.

5. The method of claim 1 wherein the ratio of potassium ions to ammonium ions in the mixed salt polyacrylate ranges from about 70:30 to 30.70.

6. The method of claim 5 wherein the ratio of potassium ions to ammonium ions in the mixed salt polyacrylate ranges from about 55:45 to about 45:55.

7. A method of increasing the yield of crops comprising contacting a plant seed with an aqueous gel comprising from about 0.4% to about 0.7% by weight of a mixed potassium and ammonium salt of a crosslinked, copolymerized or homopolymerized acrylate and covering the plant root and the aqueous gel with soil; wherein the mixed potassium and ammonium salt of a crosslinked, copolymerized or homopolymerized acrylate is prepared by mixing a monomer-solution of (A) acrylic acid neutralized 70 100 mole percent with a potassium alkali and an ammonium alkali; (B) styrene in an amount of 0% to 25% based on the weight of acrylic acid and (C) a water-miscible to water-soluble polyvinyl monomer in a combined concentration of (A), (B) and (C) of at least 30 wt. %; with water to form a mixed monomer-solution and initiating polymerization of monomers (A), (B) and (C) such that during polymerization, the exothermic heat of reaction is substantially the only heat energy used to accomplish polymerization, cross-linking and to drive off sufficient water to obtain a solid cross-linked resin having a water content of 15 percent by weight or less.

* * * * *